(12) United States Patent
Delacour

(10) Patent No.: US 7,130,033 B2
(45) Date of Patent: Oct. 31, 2006

(54) PORTABLE DEVICE FOR MEASURING THE LIGHT INTENSITY FROM AN OBJECT, AND THE USE OF SUCH A DEVICE

(75) Inventor: Jacques Delacour, Le Pradet (FR)

(73) Assignee: Optis, Toulon Cedex (FR)

( * ) Notice: Subject to any disclaimer, the term of this patent is extended or adjusted under 35 U.S.C. 154(b) by 0 days.

(21) Appl. No.: 11/241,920

(22) Filed: Oct. 4, 2005

(65) Prior Publication Data
US 2006/0023202 A1 Feb. 2, 2006

Related U.S. Application Data

(63) Continuation of application No. PCT/FR04/02555, filed on Oct. 8, 2004.

(30) Foreign Application Priority Data

Oct. 10, 2003 (FR) .................................. 03 11924

(51) Int. Cl.
*G01J 1/00* (2006.01)
(52) U.S. Cl. ...................... 356/121; 356/445
(58) Field of Classification Search ........ 356/121–123, 356/213–226, 445–448
See application file for complete search history.

(56) References Cited

U.S. PATENT DOCUMENTS

| | | | |
|---|---|---|---|
| 2,224,178 A | 12/1940 | Bitner | |
| 5,392,125 A | 2/1995 | Reisser | |
| 5,404,869 A | 4/1995 | Parkyn, Jr. et al. | |
| 5,637,873 A | 6/1997 | Davis et al. | |
| 5,757,557 A | 5/1998 | Medvedev et al. | |
| 6,018,396 A | 1/2000 | Rapaport et al. | |
| 6,819,411 B1 * | 11/2004 | Sharpe et al. | ......... 356/72 |
| 2006/0001883 A1 * | 1/2006 | Brill et al. | ......... 356/445 |

FOREIGN PATENT DOCUMENTS

| | | |
|---|---|---|
| GB | 2 041 516 | 9/1980 |
| JP | 63-140904 | 6/1988 |
| SE | 686 265 | 2/1996 |

OTHER PUBLICATIONS

J. Delacour, "Presentation of the first PLM Integrated Optical Simulation Software for the Design and Engineering of Optical Systems", Optical Design and Engineering, Proceedings of SPIE vol. 5249 (XP-002282217), Sep. 30, 2003, pp. 42-53.

* cited by examiner

*Primary Examiner*—Hoa Q. Pham
(74) *Attorney, Agent, or Firm*—Clark & Brody

(57) ABSTRACT

The invention relates to a device for measuring the light intensity of an object or object portion. The device comprises a dioptric central portion and a catadioptric peripheral portion that are independent from each other and that are suitable for delivering, from the light diffused by the object, two non-intersecting beams of the same kind, and a two-dimensional video sensor associated with an imaging device in order to obtain an image of the beams.

26 Claims, 5 Drawing Sheets

PORTABLE DEVICE FOR MEASURING THE LIGHT INTENSITY FROM AN OBJECT, AND THE USE OF SUCH A DEVICE

CROSS-REFERENCE TO RELATED APPLICATIONS

This application is a continuation of International Application No. PCT/FR2004/002555 filed Oct. 8, 2004. This PCT application was not in English as published under PCT Article 21(2).

FIELD OF THE INVENTION

The present invention relates to a device for measuring the light intensity from an object, and to the use of such a device.

The invention applies particularly but in non-limiting manner to measuring the bidirectional reflectance distribution function (BRDF) of an object or a portion of an object.

The BRDF is a mathematical function for characterizing the intensity of the light diffused by a surface when it is illuminated. The BRDF gives the quantity of light diffused as a function of the direction of observation, of the angle of incidence of the illumination, of wavelength, and of polarization.

The invention also applies to measuring the bidirectional transmittance distribution function (BTDF) and more generally the bidirectional scattering distribution function (BSDF), and to measuring intensity patterns of light sources and of bulk diffusion from materials.

BACKGROUND OF THE INVENTION

In a first known application, BRDF measurements can be used to characterize the signature of an aircraft.

For several years, BRDF measurements have been used in software for synthesizing images, for computer-assisted design (CAD), and for simulating light in order to simulate the behavior of surfaces in response to light.

For this purpose, such software makes use, e.g. in the form of a library, of real BRDF measurements performed in a laboratory on the various types of object or surface presenting optical behavior that is it desired to simulate.

In order to perform such BRDF measurements, the best known apparatuses make use of a sample of the object to be characterized. The sample must be of small dimensions, typically of the order of 10 centimeters (cm).

Such measurement apparatuses generally comprise articulated arms of large dimensions having detectors placed at their ends. Consequently they are bulky, heavy, and in practice difficult to transport.

Furthermore, the time required to acquire measurements with such apparatuses is very long, in particular because of the movements of the sensors.

Consequently, they are used exclusively in measurement laboratories and they are not adapted to taking measurements on site.

An object of the invention is to obtain a device for measuring BRDF that is of reasonable size, transportable, and thus suitable for use on site, and that enables measurements to be performed almost instantaneously, by having an acquisition time that is very short.

U.S. Pat. No. 5,637,873 (Davis) describes a BRDF measuring device suitable for use on site, e.g. to measure certain optical properties of the surface of a vehicle.

With reference to its FIG. 5, the Davis patent describes an embodiment of that device comprising a system for collecting the light reflected by an object that is to be characterized, which system is constituted by two lenses and an elliptical reflector.

More precisely, in that embodiment, the sample of the object to be characterized is placed at a first focus of the elliptical reflector, with the light reflected by the sample being focused on the second focus of the elliptical reflector.

A first lens placed at said second focus is arranged in such a manner as:
  to focus the light rays that are reflected by the sample and that are not reflected by the elliptical reflector; and
  to avoid deflecting the light rays that are reflected by the elliptical reflector.

The Davis system uses a second lens downstream from the first lens, said second lens being remarkable in that it has both a first optical portion for collimating the light rays collected by the first lens, and a second optical portion for collimating the light rays collected by the elliptical reflector. That specific second lens thus presents a discontinuity at the junction between the two above-mentioned optical portions.

That discontinuity requires the elliptical reflector and the two above-mentioned lenses to be accurately aligned, since otherwise rays reflected by the elliptical reflector become mixed in with rays focused by the first lens, and vice versa. That problem is known to the person skilled in the art under the term "cross-talk".

Japanese patent document JP 63-140904 A (Toshiba) describes a compact device for measuring the light intensity of an object, that device has a condenser lens and a reflective tubular body, with a surface array sensor being placed at the outlet thereof.

Although not described explicitly, the person skilled in the art will understand that a physical embodiment of the device requires an array of sensors of large size (typically with a diagonal of more than 50 millimeters (mm)) in order to collect all of the light diffused by the object.

The Toshiba measurement device therefore cannot use presently known standard sensors (having a diagonal of about 12.7 mm), so it is necessarily expensive to manufacture.

One solution for solving that problem is to add an afocal system between the reflective tubular body and the sensor array. That enables the outlet beam section to be reduced while conserving light collimation. An arrangement of that type is indeed used in the Davis system where it enables a small-sized video sensor to be used to observe a beam of large diameter.

However, the major drawback of that solution is that the observation plane is moved away from the reflective tubular body. Since beam divergence is never exactly zero, that leads to a corresponding degradation in resolution in the observation plane, particularly when the sample for measurement is illuminated over a large area. Consequently, the Toshiba device does not enable accurate angular measurements to be made in the intensity pattern of the diffused light.

OBJECTS AND SUMMARY OF THE INVENTION

The present invention enables the above-mentioned drawbacks to be solved.

To this end, the invention provides a device for measuring the light intensity of an object or an object portion, the device comprising:

a dioptric central portion adapted to generate a first collimated or converging beam from the light diffused by said object or object portion at an angle of inclination that is small relative to the optical axis of said dioptric central portion, when said object is placed at the object focus of said dioptric central portion;

a catadioptric peripheral portion of optical axis and of object focus that coincide respectively with said optical axis and said object focus of said dioptric central portion, said catadioptric peripheral portion being independent of said dioptric central portion, and being suitable for generating a second beam of the same kind as said first beam, from the light diffused by said object or object portion at an angle of inclination that is large relative to said optical axis, the rays of said second beam not intersecting the rays of said first beam;

a two-dimensional video sensor associated with an imaging device for obtaining an image of said first and second beams in an object plane, each ray of said beams having, in said object plane, a distance from said optical axis that is a function of said angle of inclination; and measurement means for measuring from said image the intensities of the rays of said first and second beams as a function of said angle of inclination.

The two-dimensional video sensor of the measurement device of the invention can be constituted in particular by a two-dimensional video sensor of the CCD, triple CCD, CMOS, or cathode ray tube type.

It should firstly be observed that the imaging device used in the invention can be associated with a video sensor of any format in order to collect the signal, while guaranteeing good angular resolution, which is not true of the Toshiba system described briefly above.

Furthermore, the collector system of the device of the invention, constituted by the dioptric central portion and the catadioptric peripheral portion comprises only two optical elements, thus representing a distinct advantage in terms of cost and ease of assembly compared with the Davis device which has three optical elements (an elliptical reflector, a first lens, and a special second lens).

Above all and in most advantageous manner, the dioptric central portion and the catadioptric peripheral portion of the device of the invention that serve to divide the light rays diffused by an object into two beams as a function of angle of inclination, are themselves independent and not correlated with each other.

This particularly advantageous arrangement of the device in two distinct portions, a peripheral portion and a central portion, makes it possible to obtain two beams of rays that do not intersect, and gives greater assembly tolerance on the alignment of the device, considerably reducing the above-mentioned problems of cross-talk.

It should also be observed that the measurement device of the invention uses standard components (a two-dimensional video sensor associated with an imaging device), thus making it possible to obtain a manufacturing cost that is much smaller than that of the Toshiba device described briefly above.

The imaging device associated with the two-dimensional video sensor may be constituted, in particular, by a focusing lens performing the known function of imaging the light delivered by the collector as defined above on the video sensor.

That preferred arrangement makes it possible advantageously to offset the video sensor and thus improve the resolution of the measurement device of the invention, particularly when the sample for measurement is illuminated over a large area.

This provides a measurement device presenting resolution that is much better than that of the device described in the Davis document in which the observation means are constituted by third and fourth lenses arranged to produce an afocal system serving to project the light beam directly on the video sensor.

Consequently, this preferred embodiment of the invention is particularly suited to characterizing surfaces that are granular or textured, where such measurements require illumination of a relatively large area of the object that is to be characterized.

In a variant, the imaging device may be constituted by a pinhole, particularly when the light sources illuminate the sample for measurement over a small area. This makes it possible to reduce the costs of the measurement device of the invention, to the detriment of the relative accuracy of measurements.

Two preferred variant embodiments are described below for causing the rays of the first and second beams to converge on the imaging device.

Two main variants of the measurement device of the invention can be envisaged.

In a first variant, the first and second beams coming respectively from the dioptric central portion and the catadioptric peripheral portion converge on a common focus point where the imaging device is positioned.

This first variant embodiment makes it possible to omit the field lens, and thus obtain a device that is compact.

In a second variant, the two above-mentioned beams are collimated.

In a second embodiment of this second variant, the measurement device of the invention has a field lens for causing the collimated beams to converge on a focus point, where the imaging device is positioned.

This second embodiment is very simple in design and presents a degree of flexibility in the positioning of the various optical components.

In a third variant, it is possible to use a telecentric lens. This type of lens accepts an inlet collimated light beam, which means there is no need to make the light beams converge.

In the invention, various types of dioptric central portion can be used, in particular a converging aspherical lens advantageously enabling a compact configuration to be obtained.

In another embodiment, the dioptric central portion is a lens constituted by a set of spherical lenses, thus enabling chromatic aberrations to be corrected. The accuracy of the measurements obtained thereby is greatly improved, since the illumination makes use of broad-spectrum light sources. Furthermore, the fabrication and quality control of spherical lenses are particularly easy.

In yet another embodiment, the dioptric central portion is a Fresnel lens. This component presents very small thickness (typically of millimeter order) and makes it possible to reduce the size, the weight, the quantity of materials, and the price of the measurement device of the invention.

In two first variant embodiments, the catadioptric peripheral portion may be constituted by a parabolic reflector or an elliptical reflector using specular reflection and possibly requiring the material of the reflector to be subjected reflecting treatment. These variants require little material and constitute embodiments that are inexpensive.

In a third variant embodiment, the catadioptric peripheral portion comprises:
  an inlet interface surface for the light diffused by the object or object portion at a large angle of inclination;
  a reflecting surface operating by total internal reflection; and
  an outlet interface surface for the second beam.

This third variant embodiment, which does not require reflective treatment, advantageously enables light loss to be avoided. The central and peripheral portions can then also be made as a single block.

In a preferred embodiment, the measurement device of the invention further comprises:
  at least one source adapted to generate a collimated light beam that is received by the object or object portion at a predetermined angle of incidence relative to said optical axis; and
  the measurement means are adapted to measure the intensity of the rays of the first and second beams reflected by the object as a function of said predetermined angle of incidence.

Advantageously, this embodiment enables the BRDF of an object to be measured as a function of the angle of illumination of said object.

The light source may be constituted in particular by a laser or by a laser diode.

Nevertheless, and advantageously, the light source can be constituted by associating a light-emitting diode (LED) with a field diaphragm for controlling the divergence of the light beam from the LED, an aperture diaphragm for controlling its section, and a collimator lens.

Such a light source enables an illumination beam to be obtained, that presents section and divergence that are small and predetermined.

In order to reduce cost, it is also possible to envisage a simplified source, omitting the aperture diaphragm or the collimator lens.

The light source is preferably a source of white light and the measurement means are adapted to measure the intensities of the rays of the first and second beams as a function of the wavelengths of said rays.

This embodiment that takes account of the influence of light spectrum enables the BRDF of iridescent surfaces to be characterized.

In a variant, for so-called "visual" applications, measurement means such as a color video sensor are adapted to measure the intensities of the rays of the first and second beams as a function of the primary colors (red, green, and blue) to which the human eye is sensitive.

Such a sensor makes it possible in particular to reproduce the visual appearance of the skin, of cosmetics, or of iridescent paints such as those used for certain car bodies.

For other applications, it is possible to use a set of color filters (e.g. dichroic or interference filters) that are placed in succession in front of a monochrome video camera. This makes it possible to measure BRDF wavelength by wavelength, so as to reconstitute a posteriori a complete BRDF as a function of spectrum.

Naturally, it is also possible to acquire simplified BRDFs, that are not spectrum dependent, using a monochrome sensor. The sensor may be sensitive, in particular, to wavelengths in the near infrared or the far infrared so as to acquire infrared BRDF measurements for optronic, military, and/or space applications.

In a first embodiment, the measurement device of the invention has a plurality of stationary sources of collimated light beams, each of the sources being independent of the others, and adapted to generate a beam that is received by the object that is to be characterized at an angle of incidence specific to the source.

This embodiment is particularly advantageous when the measurement device is used for measuring the BRDF of an object, given that electromagnetic theory and practical experience show that all BRDF functions depend on angle of incidence whenever an object has a highly diffusing surface.

In this embodiment, the BRDF measuring device of the invention does not have a moving source, and that constitutes a characteristic of importance for a portable device that is to perform measurements on site.

In this embodiment, each of the stationary sources is activated in its turn, with the BRDF of the object being measured as a function of the angle of incidence of the collimated beam illuminating the object.

Preferably, the measurement device of the invention has control means, in particular in the form of software, adapted to switch on the various light sources sequentially.

It should be observed at this point that the prior art Toshiba device has only one stationary light source that is adapted to emit a collimated light beam that is focused on the sample by a central converging lens at an unvarying normal angle of incidence.

The Toshiba device therefore cannot measure a BRDF function as a function of the illuminating angle of incidence as is required for iridescent paint. That important limitation is therefore removed by the present invention.

In another embodiment, a single movable light source is used that is adapted to illuminate the object or object portion that is to be characterized at different predetermined angles of incidence.

By way of example, the light source may be movable in translation on a rail.

In the second embodiment of the second above-mentioned variant, it is advantageous to use a single source that is movable in rotation about the image focus of the field lens, relative to a semi-reflecting plate positioned between said field lens and the imaging device, the semi-reflecting plate being adapted:
  to reflect the collimated light beam generated by the single source towards the object that is to be characterized; and
  to pass the first and second converging beams as delivered by the field lens.

This embodiment can be used for measuring the BRDF of an object or object portion that presents a surface that is anisotropic. Naturally, it is also possible to measure the BRDF of an object presenting an anisotropic surface using the above-described variants, by turning the device through 90° relative to the object that is to be measured.

This embodiment also makes it possible to avoid forming shadow zones in the beams, where shadow zones are due to the presence of the light sources in the beams.

The device of the invention preferably includes means for reconstituting BRDF measurements of the object or object portion as characterized in this way, and recording them on a medium.

These means for reconstituting and recording measurements on a medium enable the BRDF function to be calculated on the basis of recordings from the video sensor.

The measurement device of the invention as briefly described above in its various variants can be used, in particular, on site, in order to measure the BRDF of an object or an object portion that is difficult to access.

It can be used in particular for measuring the BRDF of the surface of a vehicle dashboard without it being necessary to cut out a sample of the dashboard for analysis.

In any event, the measurement device of the invention makes it possible to obtain intensity measurements that were impossible or very difficult to obtain with previously-known measurements devices.

The measurement device can be made at low cost and also makes it possible to acquire intensity measurements very quickly.

In entirely similar manner, the invention enables the BTDF (bidirectional transmittance distribution function), the BSDF (bidirectional scattering distribution function), or the three-dimensional diffusion to be measured of an object or object portion. In a manner that is obvious to the person skilled in the art, the light sources are then arranged in such a manner as to illuminate the object from behind, so that the object diffuses the light with intensity that is measured by device of the invention.

The invention also makes it possible to obtain intensity patterns for light-emitting devices such as LEDs, light-emitting displays, display screens, .... Under such circumstances, the measurement device does not, properly speaking, have a light source, since said light source is constituted by the object or object portion.

In a second aspect, the invention provides a computer program implementing functions of simulating the optical properties of an object or object portion, said program using light intensity measurements obtained on a real object of the same type by means of a measurement device as briefly described above.

In particular, the computer program may be software for computer-assisted design (CAD) or software for simulating light.

The invention thus makes it possible to obtain a program capable of simulating the optical properties of objects before they are made. Thus, it enables objects (roads, tunnels, ...) or structures (skin, ...) to be simulated that are difficult to access or transport into a laboratory.

BRIEF DESCRIPTION OF THE DRAWINGS

Other aspects and advantages of the present invention appear more clearly on reading the following description of particular embodiments, which description is given purely by way of non-limiting example and is made with reference to the accompanying drawings, in which.

MORE DETAILED DESCRIPTION

Figure 1:
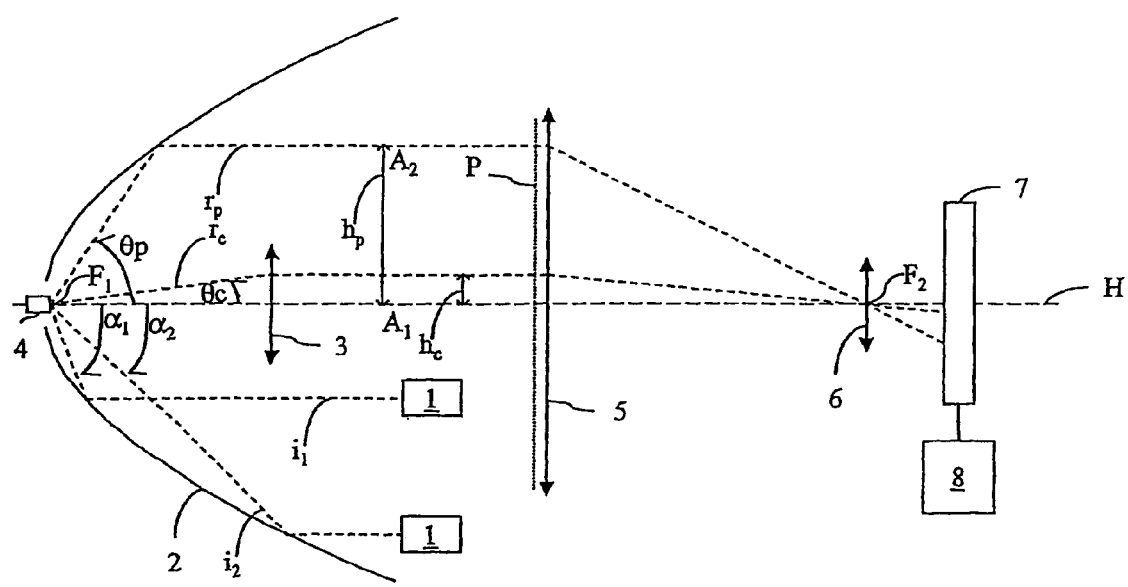
FIGS. 1 to 5 show a measurement device in accordance with the present invention in four preferred embodiments.

FIG. 1 shows a device for measuring the light intensity of an object or a portion of an object in accordance with the present invention and in a preferred embodiment.

In the embodiment described herein, the device comprises a dioptric central portion in the form of a converging aspherical lens 3 with conjugation of the focus at infinity type, and a catadioptric peripheral portion in the form of a parabolic reflector 2 pierced at its vertex.

In manner known to the person skilled in the art, the converging aspherical lens 3 may be replaced by a Fresnel lens or by a lens made up of a set of spherical lenses.

The parabolic reflector 2 makes use of specular reflection. For example it can be made of stainless steel and/or may optionally require reflective treatment, depending on the material.

The aspherical lens 3 and the parabolic reflector 2 are arranged in such a manner that their optical axes H and their focuses $F_1$ coincide.

An object or a portion of an object 4 of light intensity or BRDF that is to be measured is placed at the focus $F_1$.

This object 4 may be constituted, in particular, by a light source for which it is desired to measure intensity patterns.

In the preferred embodiment described herein, the measurement device of the invention has a plurality of collimated light-beam sources 1, e.g. five sources.

Each of these sources 1 is independent of the others, which means that it can be controlled, e.g. by software means (not shown herein), to emit or to cease emitting a light beam independently of the other sources.

In the embodiment described herein, it is assumed that each of the sources 1 emits in its turn.

For simplification purposes, two light sources 1 are shown in FIG. 1, these sources being adapted to generate respective collimated light beams represented by dashed lines $i_1$ and $i_2$.

In this figure, the collimated light beams do not pass through the aspherical lens 3. In an advantageous embodiment, some of the light beams $i_1$, $i_2$ pass through the aspherical lens 3, thus enabling the object 4 to be illuminated with an angle of incidence α relative to the optical axis H that is small.

When these collimated beams $i_1$, $i_2$ encounter the inside surface of the parabolic reflector 2, they are reflected towards the focus $F_1$ of the parabola, and consequently they are received by the object 4 placed at that point.

Each of the light beams $i_1$, $i_2$ is received by the object 4 at an angle of incidence $α_1$, $α_2$ relative to the optical axis H that is specific thereto and predetermined.

When the object 4 is illuminated by a light beam coming from a source 1, the object 4 diffuses light rays in all directions θ relative to the optical axis H.

In accordance with the invention, these light rays diffused by the object 4 and presenting an angle of inclination $θ_c$ that is small relative to the optical axis H are intercepted by the converging aspherical lens 3.

In contrast, the light rays diffused by the object 4 with an angle of inclination $θ_p$ that is large relative to the optical axis H are intercepted by the reflecting inside wall of the parabolic reflector 2.

Preferably, the angle of inclination of the light beyond which the diffuse light rays are intercept by the parabolic reflector 2 lies in the range 30° to 45°.

Beyond 45°, the converging aspherical lens 3 presents known problems of imaging and of light transmission; below 30°, the parabolic reflector becomes too bulky.

In the embodiment shown in FIG. 1, the converging aspherical lens 3 of infinite focus type conjugation, and the parabolic reflector 2, generates respective first and second collimated beams from the light diffused by the object or object portion 4, these beams being parallel to the optical axis H.

The converging aspherical lens 3 and the parabolic reflector 2 are arranged in such a manner that the rays $r_p$ and $r_c$ do not cross each other.

Rays $r_c$ and $r_p$ of the first and second beams are shown in FIG. 1.

The measurement device shown in FIG. 1 further comprises means for observing the above-mentioned first and second beams in an object plane P.

For a given ray $r_c$, $r_p$ of the first and second beams, the notation $h_c$, $h_p$ is used to denote respectively the distance between:

the point $A_2$ where said ray ($r_p$, $r_c$) intersects the object plane P; and the point $A_1$ where the optical axis H intersects the object plane P.

In a manner that is obvious to the person skilled in the art, this distance $h_c$, $h_p$ is a function of the diffusion angle $\theta_c$, $\theta_p$.

More precisely, each distance h corresponds to a diffusion angle $\theta$, and vice versa.

In the embodiment of FIG. 1, the measurement device has a field lens 5 to cause the first and second collimated beams to converge on a focus point $F_2$.

At this focus point, there is an imaging device 6 associated with a video sensor 7 to obtain an image in the object plane P of the first and second collimated beams at the field lens 5.

The imaging device 6 is typically a conventional focusing lens. Naturally, it is possible to omit a focusing lens (using the well-known "pinhole" principle), but the image that is obtained is out of focus, providing a BRDF of degraded resolution.

Figure 9:
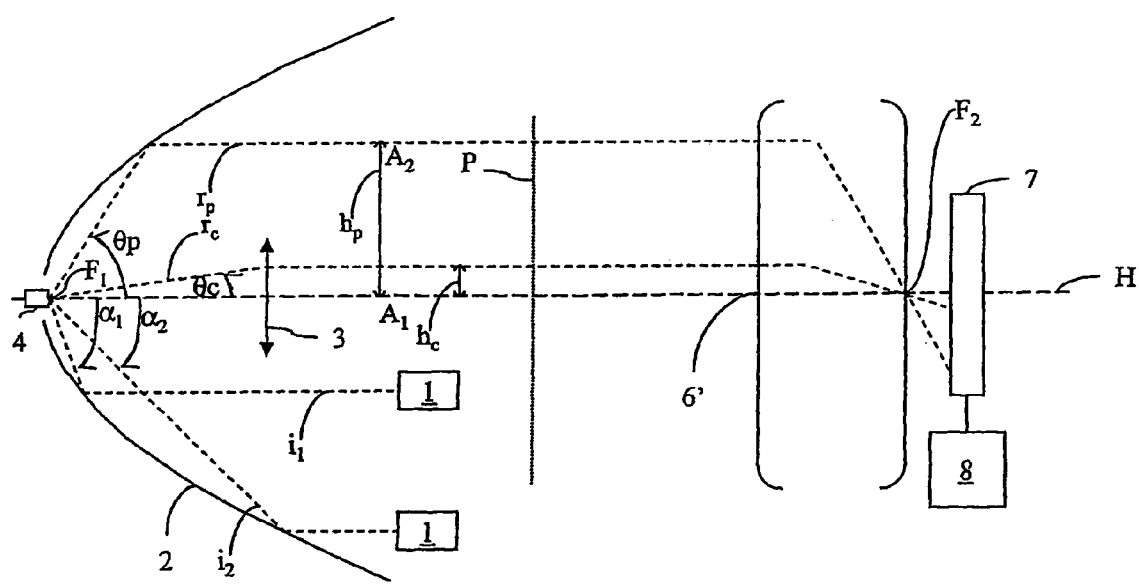
FIG. 9 shows the operation of a telecentric lens in the context of the invention.

It is also possible to use a telecentric focusing lens 6' of the type shown in FIG. 9, with the diameter of the lens 6' being greater than the size of the object to be measured. With such a lens operating with collimated light, there is no need to cause the first and second collimated beams to converge on a focusing point $F_2$. The advantage is to avoid the need to use a field lens.

Since such a lens is known to the person skilled in the art it is not described.

The image as picked up in this way is processed digitally by a computer 8, for example in order to produce a graphical representation of the light flux from the first and second beams as a function of the distance h of the rays $r_c$ and $r_p$ of these beams from the optical axis.

This digital processing thus makes it possible to reconstitute the BRDF digitally for future use in other applications, for example in light simulation software.

Figure 10:
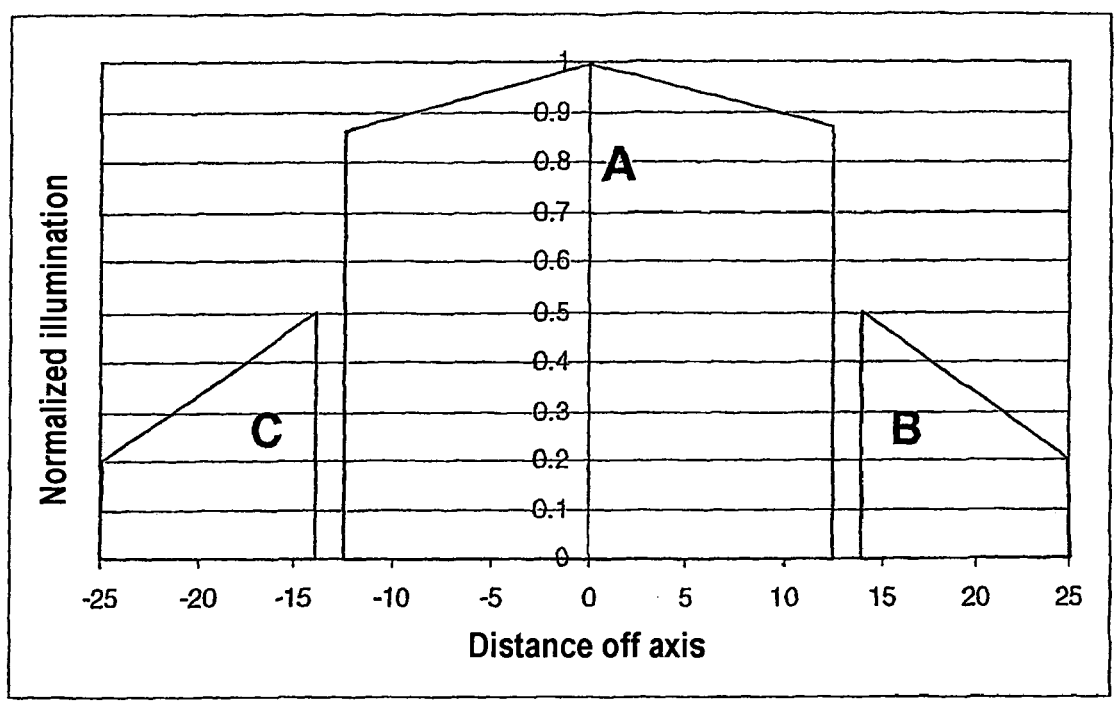
FIG. 10 is an example of a graph of light flux intensity obtained by a measurement device in accordance with the invention.

Such a chart, an example of which is given in FIG. 10, is described below. The chart comprises three portions A, B, and C.

The portion A corresponds to the light flux coming from the dioptric central portion, while the portions B and C (which are symmetrical) correspond to the light flux coming from the catadioptric peripheral portion.

It can be seen in this chart that these three portions are separate. The chart thus shows two zones of discontinuity corresponding to the physical separation between the dioptric portion and the catadioptric portion. These two zones represent the fact that the beams are not superposed. It is thus possible in advantageous manner to make use of the two beams in full.

By way of example, the video sensor 7 is a two-dimensional sensor of the CCD, triple CCD, CMOS, or cathode tube type.

In any event, this video sensor thus provides the distribution of the rays $r_c$ and $r_p$ of the first and second beams depending on their distances $h_p$, $h_c$ from the optical axis H.

As stated above, this distance distribution serves to obtain the angular distribution $\theta$ of the diffusion of these rays, since the relationship between distance h and diffusion angle $\theta$ is one to one.

The device thus makes it possible to measure the intensity of the rays $r_p$, $r_c$ of the first and second beams as a function of the angle of inclination $\theta_p$, $\theta_c$ of the light diffused by the object 4 and as a function of the angle of incidence $\alpha$ of the light beam received by the object 4 and coming from a light source 1.

In a preferred embodiment, the source 1 emits white light and the video sensor is an RGB sensor known to the person skilled in the art.

The device of the invention thus makes it possible to measure the intensity of the rays $r_p$, $r_c$ of the first and second beams as a function of the three primary colors (red, green, and blue) to which the human eye is sensitive.

This makes it possible to obtain a color BRDF, thus making it possible to reproduce the colors of an object 4 having an iridescent surface.

The measurement device described above with reference to FIG. 1 can be made in a first configuration by associating the parabolic reflector 2 that is pierced at its vertex with a converging aspherical lens 3, while keeping these two elements separate from each other.

Figure 2:
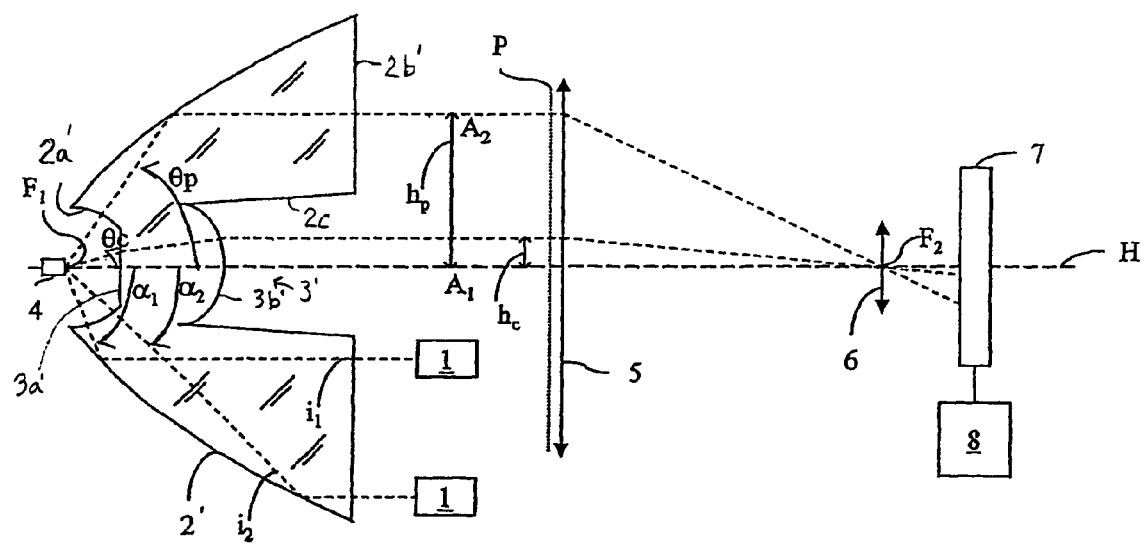

FIG. 2 shows an embodiment of the FIG. 1 device in which the parabolic reflector 2 and the converging aspherical lens 3 of FIG. 1 are made as a single block of the same transparent dielectric material, e.g. obtained by machining or by molding.

In this embodiment, the parabolic reflector 2' operates by total internal reflection. More precisely:

the converging lens 3' has a front face 3a' perpendicular to the optical axis H, and a symmetrical spherical back face 3b' centered on the focus $F_1$; and the parabolic reflector 2' has a spherical front face 2a' also centered on the focus $F_1$, and a back face 2b' perpendicular to the optical axis H.

As shown in FIG. 2, the front face 2a' of the parabolic reflector 2' extends the front face 3a' of the converging aspherical lens 3'.

Similarly, the back face 2b' is connected by a surface 2c' to the spherical back face 3b' of the converging aspherical lens 3'.

Figure 3:
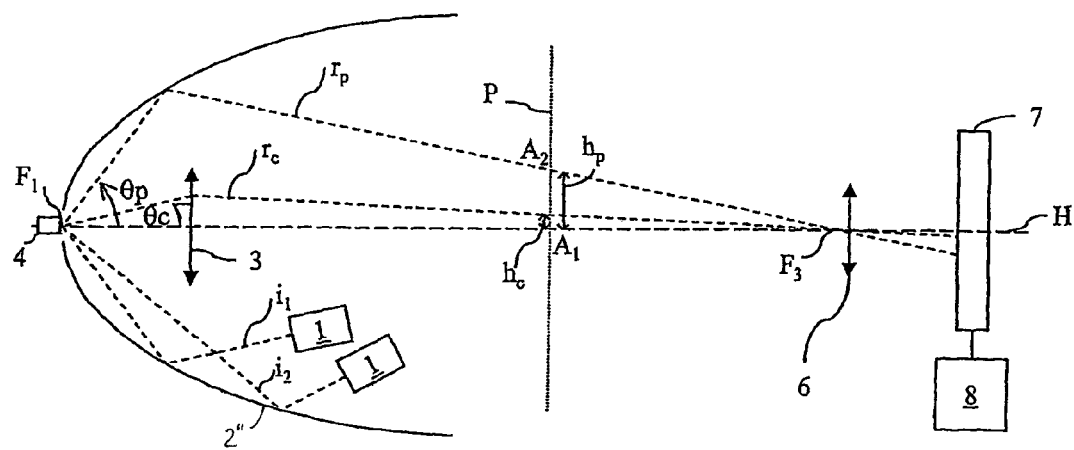

With reference to FIG. 3, there follows a description of another embodiment of the measurement device of the invention.

In this embodiment, the dioptric central portion is constituted by a converging aspherical lens 3 of real object and real image type conjugation.

In this embodiment, the catadioptric peripheral portion is constituted by an elliptical reflector 2" whose inside surface uses specular reflection.

In this embodiment, the converging aspherical lens 3 and the reflecting elliptical reflect 2" are arranged in such a manner that the rays $r_p$, $r_c$ of the first and second beams converge on a common focus point $F_3$.

In this embodiment, the measurement device does not have a field lens 5, the lens of the video sensor 7 being positioned at the focus point $F_3$.

Figure 4:
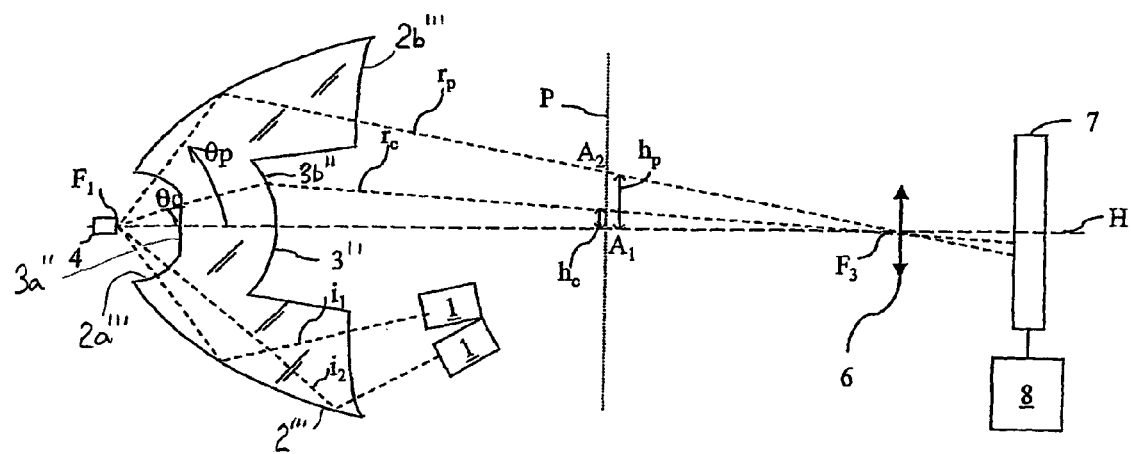

FIG. 4 is a diagram of a fourth embodiment of the measurement device of the invention.

In this embodiment, the dioptric central portion is constituted by a converging aspherical interface surface 3'''.

The catadioptric peripheral portion 2''' of this fourth embodiment comprises an inlet interface surface for the light diffused by said object or object portion when it is diffused with a large angle of inclination, a reflecting surface that operates in total internal reflection, and an outlet interface surface for said second beam.

More precisely, the catadioptric peripheral portion 2''' has a spherical front face 2a''' centered on the focus $F_1$, and a back face 2b''' that is also spherical, and centered on the focus point $F_3$.

The dioptric central portion 3'' constituted by a thick lens has a front face 3a'' perpendicular to the optical axis H, and a back face 3b'' that is aspherical.

Figure 5:
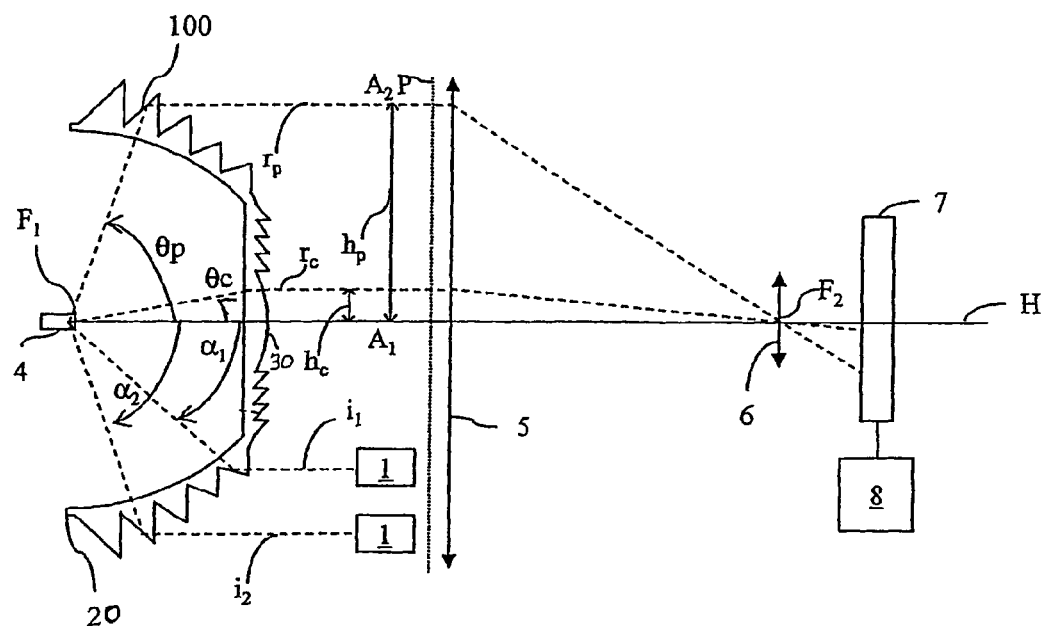

FIG. 5 is a diagram of the dioptric central portion and the catadioptric central portion of a fifth embodiment of the measurement device of the invention.

In this embodiment, the catadioptric peripheral portion is constituted by a dome 20 having an axis of revolution that coincides with the optical axis H.

The outside face of this dome is covered in microprisms 100 that act as mirrors operating in total internal reflection and locally reflecting the light beams so as to direct them towards the optical axis H. These microprisms 100 may have reflecting surfaces that are plane or parabolic. In any event, these microprisms 100 generate a collimated beam from the light diffused by the sample.

The dioptric central portion is a Fresnel lens 30 of optical function that is identical to that of the converging aspherical lens 3 of FIG. 1.

In the five embodiments described above, the collimated light-beam sources 1 may be constituted by lasers or laser diodes known to the person skilled in the art.

This embodiment is particularly suited to measuring the BRDF of an object or an object portion, when a high degree of angular resolution is required and/or when spectral information is not useful.

This applies in particular to non-iridescent surfaces for which spectral dependency is already known and is decor-related from the angle of observation.

Figure 6:
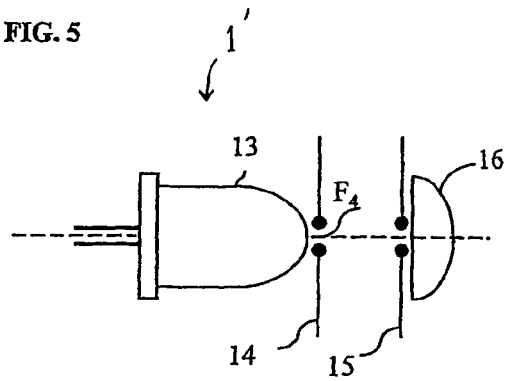
FIGS. 6 to 8 show light sources that can be used in a measurement device in accordance with the invention.

A light source 1' that is suitable for use in a measurement device in accordance with the invention is described below with reference to FIG. 6.

The light source 1' comprises an LED 13 placed upstream from a field diaphragm 14 itself positioned at the focus $F_4$ of a collimator lens 16.

In known manner, the field diaphragm serves to control the divergence of the light beam output by the LED 13.

This light source 1' also has an aperture diaphragm 15 situated close to the collimator lens 16 in order to control the aperture of the beam emitted by the LED 13.

The arrangement of the various elements constituting the source 1' serves to obtain a collimated beam possessing low divergence and limited section.

The measurement devices in accordance with the invention and as described with reference to FIGS. 1 to 4 include a plurality of stationary light sources 1, 1' each emitting a collimated light beam in its turn.

It is recalled that these light sources are not necessary when measuring intensity patterns of a light source situated at the focus $F_1$ of the dioptric central portion and the catadioptric peripheral portion.

There follows a description of two variant light sources that are movable and that are suitable for use in a measurement device of the invention.

Figure 7:
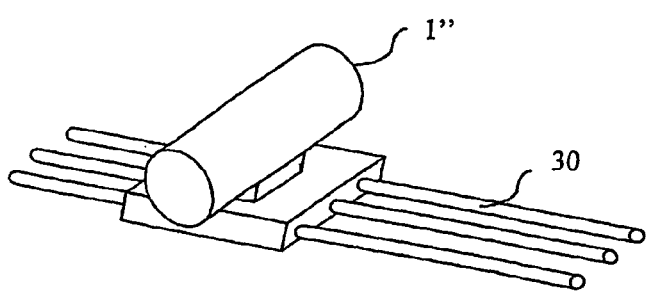

FIG. 7 shows a single light source 1'' that is movable in translation along a rail 30.

This light source 1'' can be used in particular in a measurement device of the kind shown in FIG. 1, with the rail 30 being placed perpendicularly to the optical axis H so that the movable source 1'' emits light rays parallel to said optical axis H.

Under such circumstances, the light source 1'' can occupy the positions of the various light sources 1 described above with reference to FIG. 1.

This movable light source 1'' can also be used in the embodiment of FIG. 2, on the sole condition that the rail 30 is arranged in such a manner that the light beams emitted by the source 1'' are directed away from the focus point $F_3$.

In any event, the movable light source 1'' can be moved along the rail 30 by means that are not shown herein.

This embodiment is particularly advantageous since, by moving the source 1'' along the rail 30, it enables the object 4 to be illuminated under a variety of angles of incidence α.

Figure 8:
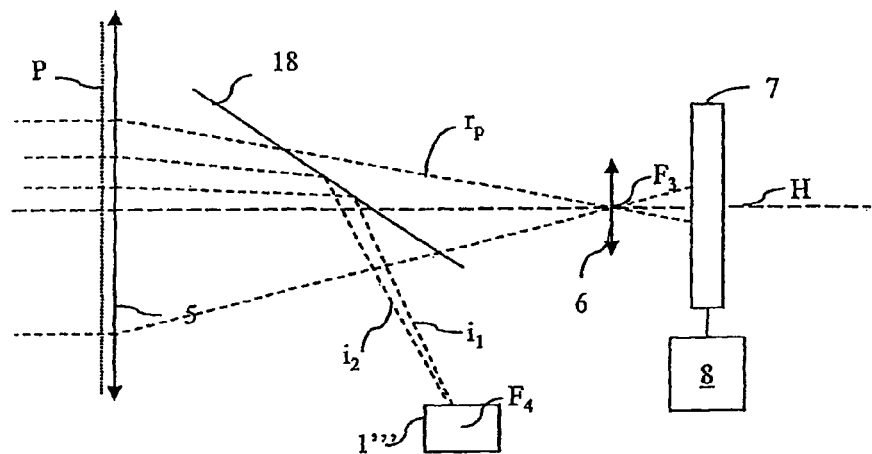

FIG. 8 shows a variant single movable source 1''' suitable for use in a device in accordance with the invention when the dioptric and catadioptric central portions and generate first and second collimated beams, as in the embodiments of FIG. 1 or 2, for example.

As described above, such an embodiment has a field lens 5 adapted to converge the rays $r_c$ and $r_p$ of the first and second beams towards a focus point $F_3$.

In the variant described here, the measurement device of the invention has a semi-reflective plate 18 positioned between said field lens 5 and the imaging device 6.

This semi-reflective plate 18 allows the rays $r_c$, $r_p$ of the first and second beams to pass and converge on the imaging device 6.

In this embodiment, the light source 1''' is turnable about the image focus $F_4$ of the field lens 5 relative to the semi-reflective plate 18.

In this arrangement, the semi-reflective plate 18 reflects the collimated beam generated by the single source 1''' towards the object 4.

More precisely, the angle of incidence α of the light beam received by the object 4 depends directly on the orientation of the light source 1''' relative to the semi-reflective plate 18.

This embodiment is particularly advantageous since it can be used for measuring the BRDF of an object or an object portion 4 that presents a surface that is anisotropic.

In a variant, it is possible to use a stationary light source associated with a mirror that can be turned about two axes, the mirror being centered on the image focus $F_4$ of the field lens 5, the light source emitting a collimated light beam that is reflected on the center of the mirror.

Clearly, the single movable source as described above with reference to FIG. 8 can be used in the embodiments of the measurement device of the invention as shown in FIGS. 3 and 4. Under such circumstances, the person skilled in the art will understand that the field lens 5 is not used.

The various embodiments of the measurement device of the invention as described above can be use for measuring the BRDF of an object or an object portion as a function of the angle of illumination α of the object, of the direction of observation θ of the object, and of the polarization of the light when a white source is used in combination with an RGB color video camera.

These embodiments of the invention all present the advantage of being particularly compact because of the association of the dioptric central portion and the catadioptric peripheral portion.

They also make it possible to measure all of the light emitted in a half-space.

The preferred embodiment described with reference to FIG. 7 also enables the BRDF of an iridescent surface to be measured, without it being necessary to move the device relative to the object that is to be characterized.

Furthermore, and in a manner that is obvious to the person skilled in the art, the measurement device of the invention can be used for measuring the BTDF of a translucent surface. Under such circumstances, the light intensity that is measured is that which is transmitted by the object or the object portion to be characterized, and not the light that is reflected.

These various embodiments thus make it possible to measure the BRDF of objects or surfaces that are difficult to access, or for which it is desirable not to take a sample.

A measurement device of the invention is very simple to use since it suffices to scan the object that is to be characterized. The intensity measurement data that is picked up can then be processed digitally, e.g. by a computer program in order to reconstitute a BRDF function. This BRDF function can then be used a posteriori in CAD, image synthesis, or light simulation software.

These computer programs can thus provide particularly realistic simulation of the optical properties of an object or of the behavior of an object relative to light.

A preferred use of the invention thus lies in the field of software for computer-assisted design and for simulating light, since it enables the optical behavior of an object to be predicted very realistically before it is manufactured.

What is claimed is:

1. A device for measuring the light intensity of an object or an object portion, the device comprising:
    a dioptric central portion adapted to generate a first collimated beam from the light diffused by said object or object portion at an angle of inclination that is small relative to the optical axis of said dioptric central portion, when said object is placed at the object focus of said dioptric central portion; and
    a parabolic reflector of optical axis and of object focus that coincide respectively with said optical axis and said object focus of said dioptric central portion, said reflector being independent of said dioptric central portion, and being suitable for generating a second collimated beam from the light diffused by said object or object portion at an angle of inclination that is large relative to said optical axis, the rays of said second beam not intersecting the rays of said first beam in the object plane situated at the outlet of the reflector and the dioptric central portion;
    said measurement device further comprising:
        an imaging device and a two-dimensional video sensor associated with the imaging device, the imaging device for obtaining an image of said first and second beams in an object plane, each ray of said beams having, in said object plane, a distance from said optical axis that is a function of said angle of inclination; and
        measurement means for measuring from said image the intensities of the rays of said first and second beams as a function of said angle of inclination.

2. A measurement device according to claim 1, wherein said first and second beams are collimated beams and the device further comprises a field lens to cause said beams to converge on a focus point where the imaging device is positioned.

3. A measurement device according to claim 1, wherein the first and second beams are collimated beams, and wherein said imaging device is a telecentric focusing lens.

4. A measurement device according to claim 1, wherein said dioptric central portion is a converging aspherical lens, a lens made up of a set of spherical lenses, or a Fresnel lens.

5. A measurement device according to claim 1, further comprising:
    at least one source adapted to generate a collimated light beam received by said object or object portion at an angle of incidence that is predetermined relative to said optical axis; and wherein
    said measurement means are adapted to measure the intensity of the rays of said first and second beams as reflected by said object or object portion as a function of said predetermined angle of incidence.

6. A measurement device according to claim 5, wherein said at least one source is a laser or a laser diode.

7. A measurement device according to claim 5, wherein, in order to generate said collimated light beam, said at least one source comprises an LED, and optionally a field diaphragm situated at the focus of a collimator lens and an aperture diaphragm situated close to said collimator lens.

8. A measurement device according to claim 5, wherein said at least one light source is a source of white light, and said measurement means are adapted to measure the intensity of the rays of the first and second beams at at least one of the wavelengths of said rays.

9. A measurement device according to claim 8, wherein said measurement means are adapted to measure the intensities of the rays of the first and second beams as a function of the primary colors (red, green, blue) to which the eye is sensitive.

10. A measurement device according to claim 5, including a plurality of stationary sources of collimated light beams, each of the sources being independent of the others, and each being adapted to generate a beam that is received by said object or object portion at an angle of incidence specific to the source.

11. A measurement device according to claim 10, further comprising control means suitable for switching on said light sources in sequence.

12. A measurement device according to claim 5, comprising a single movable light source adapted to generate a light beam that is received by said object or object portion at a predetermined variable angle of incidence.

13. A measurement device according to claim 12, wherein said single light source is movable in translation on a rail.

14. A measurement device according to claim 13, wherein said first and second beams are collimated beams and the device further comprises a field lens to cause said beams to converge on a focus point where the imaging device is positioned, and wherein said single light source is movable to turn about the image focus of said field lens relative to a semi-reflective plate positioned between said field lens and said observation means, said semi-reflecting plate being adapted:
    to reflect said collimated light beam generated by said single source towards said object or object portion; and
    to pass said first and second converging beams delivered by said field lens.

15. A measurement device according to claim 1, further comprising means for reconstituting measurements of the BRDF, the BTDF, or the BSDF of said object or object portion and for recording them on a medium.

16. The use of a measurement device according to claim 1 for measuring the BRDF, the BTDF, or the BSDF of an object or object portion, in particular on-site when the object or object portion is difficult to access.

17. The use of a measurement device according to claim 16 to measure the BRDF of an object or an object portion presenting a surface that is anisotropic.

18. The use of a measurement device according to claim 1, for measuring intensity patterns of a light source constituted by said object.

19. A computer program for performing functions of simulating the optical properties of an object or an object portion, the program using light intensity measurements obtained from a real object of the same type with a measurement device in accordance with claim 1.

20. A computer program according to claim 19, said program being a computer-assisted design program or a light simulation program.

21. A device for measuring the light intensity of an object or an object portion, the device comprising:
   a dioptric central portion adapted to generate a first collimated beam from the light diffused by said object or object portion at an angle of inclination that is small relative to the optical axis of said dioptric central portion, when said object is placed at the object focus of said dioptric central portion; and
   a catadioptric peripheral portion of optical axis and of object focus that coincide respectively with said optical axis and said object focus of said dioptric central portion, said catadioptric peripheral portion being independent of said dioptric central portion, and being suitable for generating a second collimated beam from the light diffused by said object or object portion at an angle of inclination that is large relative to said optical axis, the rays of said second beam not intersecting the rays of said first beam in the object plane situated at the outlet of the catadioptric peripheral portion and the dioptric central portion;
   said measurement device further comprising:
      an imaging device and a two-dimensional video sensor associated with the imaging device, the imaging device for obtaining an image of said first and second beams in an object plane, each ray of said beams having, in said object plane, a distance from said optical axis that is a function of said angle of inclination; and
      measurement means for measuring from said image the intensities of the rays of said first and second beams as a function of said angle of inclination.

22. A measurement device according to claim 21, wherein said first and second beams are collimated beams and the device further comprises a field lens to cause said beams to converge on a focus point where the imaging device is positioned.

23. A device for measuring the light intensity of an object or an object portion, the device comprising:
   a dioptric central portion adapted to generate a first converging beam from the light diffused by said object or object portion at an angle of inclination that is small relative to the optical axis of said dioptric central portion, when said object is placed at the object point of said dioptric central portion; and
   an elliptical reflector of optical axis and of object focus that coincide respectively with said optical axis and said object point of said dioptric central portion, said elliptical reflector being suitable for generating a second converging beam from the light diffused by said object or object portion at an angle of inclination that is large relative to said optical axis when said object is placed at said object focus, and in which said dioptric central portion and said elliptical reflector are arranged in such a manner that the rays of the first and second beams converge on a common focus point, said reflector being independent of said dioptric central portion, the rays of said second beam not intersecting the rays of said first beam in the object plane situated at the outlet of the elliptical reflector and the dioptric central portion;
   said measurement device further comprising:
      an imaging device and a two-dimensional video sensor associated with the imaging device, the imaging device for obtaining an image of said first and second beams in an object plane, each ray of said beams having, in said object plane, a distance from said optical axis that is a function of said angle of inclination; and
      measurement means for measuring from said image the intensities of the rays of said first and second beams as a function of said angle of inclination.

24. A measurement device according to claim 23, wherein said first and second beams converge on a common focus point, the imaging device of said video sensor being positioned at said focus point.

25. A device for measuring the light intensity of an object or an object portion, the device comprising:
   a dioptric central portion constituted by a converging aspherical interface surface adapted to generate a first converging beam from the light diffused by said object or object portion at an angle of inclination that is small relative to the optical axis of said interface surface; and
   a catadioptric peripheral portion of optical axis and of object focus that coincide respectively with said optical axis and said object focus of said dioptric central portion, said catadioptric peripheral portion being independent of said dioptric central portion, and being suitable for generating a second converging beam from the light diffused by said object or object portion at an angle of inclination that is large relative to said optical axis, the rays of said second beam not intersecting the rays of said first beam in the object plane situated at the outlet of the catadioptric peripheral portion and the dioptric central portion;
   said measurement device further comprising:
      an imaging device and a two-dimensional video sensor associated with the imaging device, the imaging device for obtaining an image of said first and second for obtaining an image of said first and second beams in an object plane, each ray of said beams having, in said object plane, a distance from said optical axis that is a function of said angle of inclination; and
      measurement means for measuring from said image the intensities of the rays of said first and second beams as a function of said angle of inclination.

26. A measurement device according to claim 25, wherein said first and second beams converge on a common focus point, the imaging device of said video sensor being positioned at said focus point.

* * * * *